United States Patent
Yu et al.

(10) Patent No.: US 8,705,822 B2
(45) Date of Patent: Apr. 22, 2014

(54) METHOD FOR CREATING IMAGES INDICATING MATERIAL DECOMPOSITION IN DUAL ENERGY, DUAL SOURCE HELICAL COMPUTED TOMOGRAPHY

(75) Inventors: Lifeng Yu, Rochester, MN (US); Cynthia H. McCollough, Byron, MN (US)

(73) Assignee: MAYO Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/059,579

(22) PCT Filed: Sep. 2, 2009

(86) PCT No.: PCT/US2009/055706
§ 371 (c)(1),
(2), (4) Date: Apr. 26, 2011

(87) PCT Pub. No.: WO2010/028027
PCT Pub. Date: Mar. 11, 2010

(65) Prior Publication Data
US 2011/0188725 A1      Aug. 4, 2011

Related U.S. Application Data

(60) Provisional application No. 61/093,748, filed on Sep. 3, 2008.

(51) Int. Cl.
*G06T 11/00* (2006.01)
*G01N 29/00* (2006.01)

(52) U.S. Cl.
USPC .............................................. 382/128; 378/5

(58) Field of Classification Search
None
See application file for complete search history.

(56) References Cited

U.S. PATENT DOCUMENTS

| 7,298,812 B2 * | 11/2007 | Tkaczyk et al. ............. 378/5 |
| 2004/0081280 A1 * | 4/2004 | Avinash ............. 378/98.9 |
| 2004/0174960 A1 * | 9/2004 | Hsieh et al. ............. 378/210 |

(Continued)

FOREIGN PATENT DOCUMENTS

WO   WO 2007/082650 A2 *   7/2007

OTHER PUBLICATIONS

Hsieh et al., "An iterative approach to the beam hardening correction in cone beam CT", Med Phys. 27 (1), Jan. 2000, p. 23-29.*

(Continued)

*Primary Examiner* — Tahmina Ansari
(74) *Attorney, Agent, or Firm* — Quarles & Brady, LLP

(57) ABSTRACT

A system and method for the accurate quantitative evaluation of dual-energy computed tomography (CT) projection data that is acquired in a dual-source helical scan includes employing a dual-source z-axis helical interpolation method. The method includes transforming the two helical projection data sets, where corresponding projections of high- and low-energy data sets are shifted with respect to one another by 90 degrees or another angle, into corresponding non-helical projection data sets. A dual-source helical interpolation algorithm allows for projection space dual-energy processing by realigning the high- and low-energy datasets based on the z-axis interpolation. This algorithm may be implemented using a variety of interpolation schemes and can be extended from single slice to multi-slice data acquisitions. Subsequent to the registration of the non-helical projection data sets, projection space processing allows for accurate material quantification and virtual monochromatic images in which beam hardening artifacts have been substantially suppressed.

16 Claims, 4 Drawing Sheets

(56) References Cited

U.S. PATENT DOCUMENTS

| | | | |
|---|---|---|---|
| 2004/0184574 A1 | 9/2004 | Wu et al. | |
| 2006/0109949 A1 | 5/2006 | Tkaczyk et al. | |
| 2006/0133562 A1* | 6/2006 | Heuscher et al. | 378/4 |
| 2006/0159223 A1* | 7/2006 | Wu et al. | 378/18 |
| 2007/0237288 A1* | 10/2007 | Tkaczyk et al. | 378/5 |
| 2007/0274581 A1* | 11/2007 | Wu et al. | 382/131 |
| 2008/0310598 A1* | 12/2008 | Zhang et al. | 378/207 |
| 2009/0028288 A1* | 1/2009 | Horiuchi et al. | 378/4 |
| 2009/0110259 A1* | 4/2009 | Yin et al. | 382/132 |
| 2009/0169051 A1* | 7/2009 | Ioannou et al. | 382/100 |
| 2010/0166273 A1* | 7/2010 | Wismuller | 382/131 |
| 2011/0188725 A1* | 8/2011 | Yu et al. | 382/131 |

OTHER PUBLICATIONS

"Helix" Wikipedia article, Date retrieved Jul. 11, 2013, From http://en.wikipedia.org/wiki/Helix.*

"Spiral computed tomography", Wikipedia article, Date retrieved Jul. 11, 2013, From http://en.wikipedia.org/wiki/Spiral_computed_tomography.*

The International Search Report as mailed on Oct. 30, 2009, in connection with PCT/US2009/055706.

* cited by examiner

METHOD FOR CREATING IMAGES INDICATING MATERIAL DECOMPOSITION IN DUAL ENERGY, DUAL SOURCE HELICAL COMPUTED TOMOGRAPHY

CROSS-REFERENCE TO RELATED APPLICATIONS

This application is based on, claims the benefit of, and herein incorporates by reference in their entirety, PCT International Application PCT/US2009/055706 filed on Sep. 2, 2009 and U.S. Provisional Patent Application Ser. No. 61/093,748 filed on Sep. 3, 2008, and entitled "METHOD FOR RECONSTRUCTION IN DUAL ENERGY, DUAL SOURCE HELICAL COMPUTED TOMOGRAPHY."

STATEMENT REGARDING FEDERALLY SPONSORED RESEARCH

This invention was made with United States government support awarded by the following agency: National Institute of Biomedical Imaging and Bioengineering EB07986. The United States Government has certain rights in this invention.

BACKGROUND OF THE INVENTION

The present invention relates to computed tomography imaging systems and methods and, more particularly, the invention relates to dual-source, dual-energy computed tomography.

In a current computed tomography system, an x-ray source projects a fan-shaped beam that is collimated to lie within an X-Y plane of a Cartesian coordinate system, termed the "imaging plane." The x-ray beam passes through the object being imaged, such as a medical patient, and impinges upon an array of radiation detectors. The intensity of the radiation received by each detector is dependent upon the attenuation of the x-ray beam by the object and each detector produces a separate electrical signal that relates to the attenuation of the beam. The linear attenuation coefficient is the parameter that describes how the intensity of the x-rays changes when passing through an object. Often, the "mass attenuation coefficient" is utilized because it does not change with the density of the material. The attenuation measurements from all the detectors are acquired separately to produce the transmission map.

The source and detector array in a conventional CT system are rotated on a gantry within the imaging plane and around the object so that the projection angle at which the x-ray beam intersects the object constantly changes. A group of x-ray attenuation measurements from the detector array at a given angle is referred to as a "view" and a "scan" of the object. These views are collected to form a set of views made at different angular orientations during one or several revolutions of the x-ray source and detector. In a two dimensional (2D) scan, data is processed to construct an image that corresponds to a 2D slice taken through the object. The prevailing method for reconstructing an image from 2D data is referred to in the art as the filtered backprojection (FBP) technique. This process converts the attenuation measurements from a scan into integers called "CT numbers" or "Hounsfield units", which are used to control the brightness of a corresponding pixel on a display.

The term "generation" is used in CT to describe successively commercially available types of CT systems utilizing different modes of scanning motion and x-ray detection. More specifically, each generation is characterized by a particular geometry of scanning motion, scanning time, shape of the x-ray beam, and detector system.

The first generation utilized a single pencil x-ray beam and a single scintillation crystal-photomultiplier tube detector for each tomographic slice. After a single linear motion or traversal of the x-ray tube and detector, during which time 160 separate x-ray attenuation or detector readings are typically taken, the x-ray tube and detector are rotated through 1 degree and another linear scan is performed to acquire another view. This is repeated typically to acquire 180 views.

A second generation of CT systems was developed to shorten the scanning times by gathering data more quickly. In these units a modified fan beam is utilized, which may include anywhere from three to 52 individual collimated x-ray beams and an equal number of detectors. Individual beams resemble the single beam of a first generation scanner. However, a collection of from three to 52 of these beams contiguous to one another allows multiple adjacent cores of tissue to be examined simultaneously. The configuration of these contiguous cores of tissue resembles a fan, with the thickness of the fan material determined by the collimation of the beam and, in turn, determining the slice thickness. Because of the angular difference of each beam relative to the others, several different angular views through the body slice are examined simultaneously. Superimposed on this is a linear translation or scan of the x-ray tube and detectors through the body slice. Thus, at the end of a single translational scan, during which time 160 readings may be made by each detector, the total number of readings obtained is equal to the number of detectors times 160. The increment of angular rotation between views can be significantly larger than with a first generation unit, up to as much as 36 degrees. Thus, the number of distinct rotations of the scanning apparatus can be significantly reduced, with a coincidental reduction in scanning time. By gathering more data per translation, fewer translations are needed.

To obtain even faster scanning times it is necessary to eliminate the complex translational-rotational motion of the first two generations. Third generation scanners therefore use a much wider, "divergent" fan beam. In fact, the angle of the beam may be wide enough to encompass most or all of an entire patient section without the need for a linear translation of the x-ray tube and detectors. As in the first two generations, the detectors, now in the form of a large array, are rigidly aligned relative to the x-ray beam, and there are no translational motions at all. The tube and detector array are synchronously rotated about the patient through an angle of 180-360 degrees. Thus, there is only one type of motion, allowing a much faster scanning time to be achieved. After one rotation, a single tomographic section is obtained.

Fourth generation scanners also feature a divergent fan beam similar to the third generation CT system. As before, the x-ray tube rotates through 360 degrees without having to make any translational motion. However, unlike in the other scanners, the detectors are not aligned rigidly relative to the x-ray beam. In this system only the x-ray tube rotates. A large ring of detectors are fixed in an outer circle in the scanning plane. The necessity of rotating only the tube, but not the detectors, allows faster scan time.

With the development of detector technology, multi-detector row CT that allows simultaneous data acquisition of multiple slices has been widely used in clinical practice. The number of slices has evolved from 4 to 320, which allows extremely fast scanning speed. Each x-ray projection view becomes a cone-beam shape instead of a fan-beam shape. The image reconstruction from cone-beam data acquisition has been a challenging problem.

Exact reconstruction methods have been proposed and further developed for both a helical x-ray source trajectory and more general source trajectories. A mathematically exact and shift-invariant FBP reconstruction formula was proposed for the helical/spiral source trajectory by A. Katsevich, "Theoretically exact filtered backprojection-type inversion algorithm for spiral CT," SIAM (Soc. Ind. Appl. Math.) J. Appl. Math. 62, 2012-2026 (2002).

Dual energy x-ray imaging systems acquire images of the subject at two different x-ray energy levels. This can be achieved with a conventional third generation CT system by alternately acquiring views using two different x-ray tube anode voltages. Alternatively, two separate x-ray sources with associated detector arrays may be operated simultaneously during a scan at two different energy levels. In either case, two registered images of the subject are acquired at two prescribed energy levels.

The measurement of an x-ray transmission map attenuated by a subject at two distinct energy bands is often used to determine material-specific information of an imaged subject. This is based upon that fact that, in general, attenuation is a function of x-ray energy according to two attenuation mechanisms: photoelectric absorption and Compton scattering. These two mechanisms differ among materials of different atomic numbers. For this reason, measurements at two energies can be used to distinguish between two different basis materials. Dual energy x-ray techniques can be used, for example, to separate bony tissue from soft tissue in medical imaging, to quantitatively measure bone density, to remove plaque from vascular images, and to distinguish between different types of kidney stones.

Currently, one of the conventional methods employed to determine the effective atomic number and density of the material from a dual energy CT measurement is described, for example, in L. A. Lehmann, et al., "Generalized Image Combinations in Dual KVP Digital Radiography," Med Phys (1981); 8:659-667. This method is further summarized and implemented by W. A. Kalendar, et al., in "Evaluation of a prototype dual-energy computed tomographic apparatus. I. Phantom studies." Med Phys. 1986; 13(3):334-339. In general, the linear attenuation coefficient, $\mu(r,E)$, can be expressed as a linear combination of the mass attenuation coefficients of two so-called basis materials, as follows:

$$\mu(r, E) = \left(\frac{\mu}{\rho}\right)_1 (E) \cdot \rho_1(r) + \left(\frac{\mu}{\rho}\right)_2 (E) \cdot \rho_2(r), \quad (1)$$

where r is the spatial location at which a measurement is made, E is the energy at which a measurement is made, $\rho_i(r)$ is the decomposition coefficient of the $i^{th}$ basis material, and $$\left(\frac{\mu}{\rho}\right)_i (E)$$

is the mass attenuation coefficient of the $i^{th}$ basis material.

This method is commonly referred to as the basis-material method. In this method, CT measurements are needed at two energy levels (high and low) to solve the two unknowns $\rho_1(r)$ and $\rho_2(r)$. The detected signals for these two energy levels can be expressed as:

$$I_k = \int S_k(E) \cdot D(E) \cdot E \cdot e^{-\left[\left(\frac{\mu}{\rho}\right)_1 (E) \cdot L_1 + \left(\frac{\mu}{\rho}\right)_2 (E) \cdot L_2\right]} dE, \quad (2)$$

where $S_k(E)$ is the x-ray spectrum for the $k^{th}$ x-ray energy, $D(E)$ is the detector response, $L_1 = \int dl \cdot \rho_1(r)$, and $L_2 = \int dl \cdot \rho_2(r)$, which represent the line integral of the densities of the two basis materials, respectively.

Instead of solving the above integral equation directly, the basis-material decomposition method typically uses a table lookup procedure to solve equation (2) in order to determine $L_1$ and $L_2$. Conventional reconstruction methods are subsequently used to produce density maps of the two basis materials. Utilizing the information contained in the density maps of the two basis materials, the linear attenuation coefficient of the subject, $\mu(r,E)$, is determined. Monochromatic images can thus be synthesized by using the linear combination suggested by Eq. (1).

Accordingly, the basis-material method is a practical method to employ in a clinical setting when using dual-energy CT. The decomposition coefficients, $\rho_i(r)$, can be interpreted as components in a two-dimensional vector space, with the basis materials defining the basis vectors. The above-described basis-material method belongs to the "pre-reconstruction" class of quantitative CT methods. That is, the method is performed with raw data, or "projection space data," prior to reconstruction.

Currently, dual-source CT (DSCT) scanners with two source-detector pairs that are 90 degrees apart are used for many dual-energy applications. However, when operating in helical mode, the projection data acquired by the two source-detector pairs are not coincident with each other. As a result, the acquired dual-energy data cannot be processed prior to image reconstruction. This presents many limitations on the quantitative evaluation of materials when operating a DSCT scanner at dual-energies and in helical mode.

DSCT scanners, with orthogonal x-ray source-detector pairs, generally force image reconstruction to occur prior to dual-energy processing, as a result of the 90 degree offset between corresponding projections in the high- and low-energy image data sets. For axial CT acquisitions, shifting of one data set by 90 degrees would allow projection space dual-energy processing, since all of the projections are coplanar. However, in helical mode, the projection data from the two sources are not aligned with any other projections at any point in the dataset due to the continuous motion of the object along the z-axis. This precludes projection space dual-energy processing and represents a major limitation in the dual-source approach to dual-energy helical CT.

Furthermore, since helical, dual-energy data cannot be readily processed prior to image reconstruction, the resultant images suffer from beam hardening errors. That is, in non-DSCT systems, once the dual-energy algorithm decomposes the data into two components of the two basis materials (or atomic number and density), monochromatic images can be constructed at any specific photon energy. These monochromatic images are substantially improved because beam-hardening errors are substantially corrected.

Therefore, it would be advantageous to have a system and method for utilizing DSCT systems, for example in helical mode or other modes, more efficiently and without the resultant images suffering from beam-hardening artifacts.

SUMMARY OF THE INVENTION

The present invention overcomes the aforementioned drawbacks by providing a method for projection-space processing of data acquired by a dual-energy, dual-source computed tomography imaging system, for example, operating in a helical scan mode. More specifically, the present invention provides a method for the dual-energy processing of data in projection space for dual-source helical CT by first transforming the helical data acquired by both x-ray sources to two corresponding sets of non-helical projection data that are coincident with each other. The transformed non-helical data sets are subsequently used in basis-material decomposition methods to obtain monochromatic images and material-specific information.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
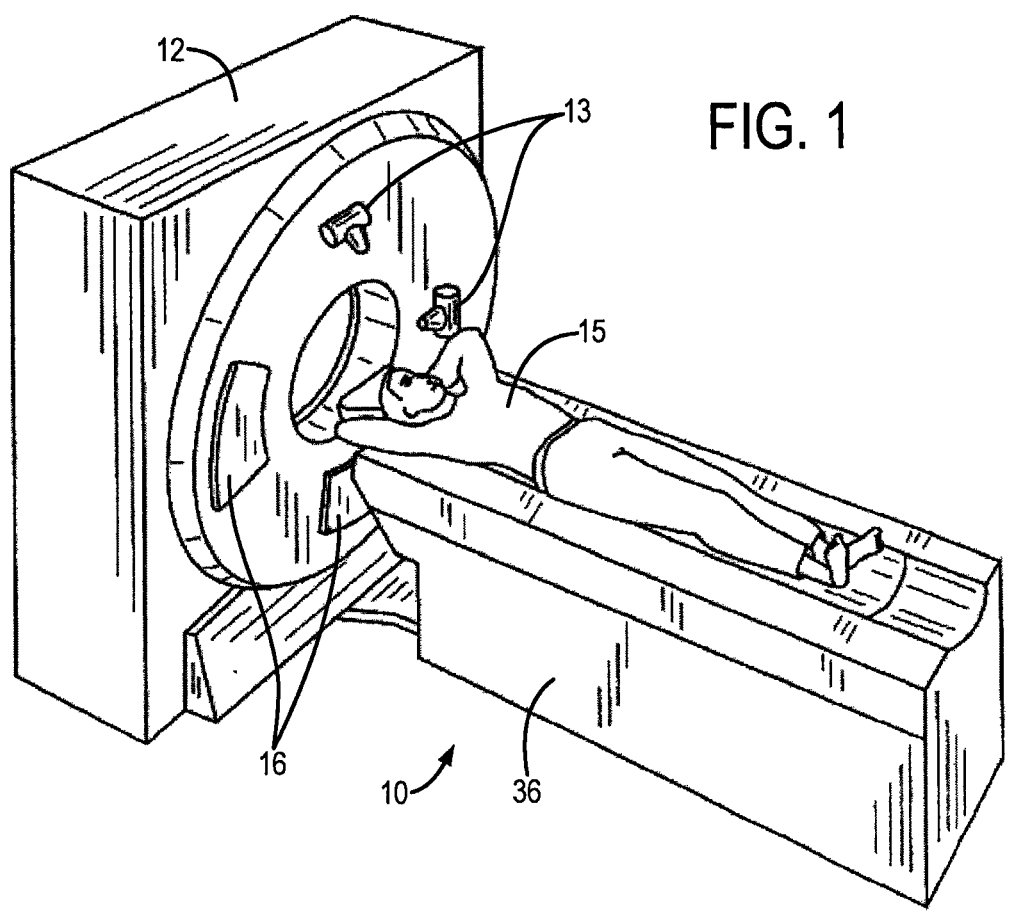
FIG. 1 is a perspective view of a computed tomography (CT) imaging system in which the present invention may be employed.
Figure 2:
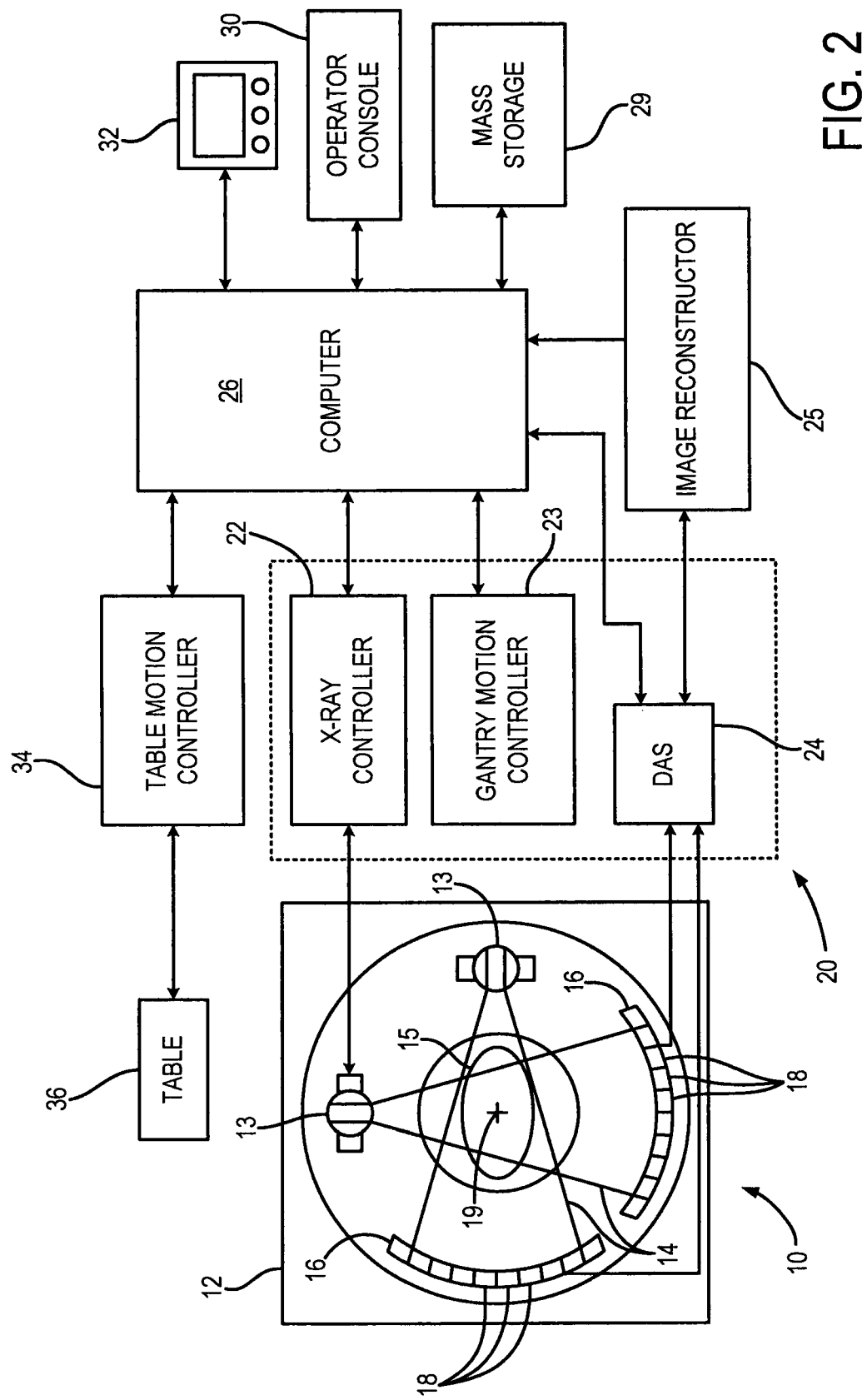
FIG. 2 is a block schematic diagram of the CT imaging system of FIG. 1.

With initial reference to FIGS. 1 and 2, a computed tomography (CT) imaging system 10 includes a gantry 12 representative of a "third generation" CT scanner. The gantry 12 has a pair of x-ray sources 13 that each project a fan beam or cone beam of x-rays 14 toward a detector array 16 on the opposite side of the gantry. Collectively, each x-ray source 13 and corresponding detector array 16 are referred to as a source-detector pair. More specifically, and in one configuration, each source-detector pair is coupled to the gantry 12 and angularly displaced about the gantry 12 so that an angle of 90 degrees exists therebetween. The detector array 16 is formed by a number of detector elements 18, which together sense the projected x-rays that pass through a medical patient 15. Each detector element 18 produces an electrical signal that represents the intensity of an impinging x-ray beam and, hence, the attenuation of the beam as it passes through the patient. During a scan to acquire x-ray projection data, the gantry 12 and the components mounted thereon rotate about a center of rotation 19 located within the patient 15 to acquire attenuation data for each of the two x-ray sources.

The rotation of the gantry and the operation of the x-ray sources 13 are governed by a control mechanism 20 of the CT system. The control mechanism 20 includes an x-ray controller 22 that provides power and timing signals to the x-ray sources 13 and a gantry motor controller 23 that controls the rotational speed and position of the gantry 12. A data acquisition system (DAS) 24 in the control mechanism 20 samples analog data from detector elements 18 in each detector array and converts the data to digital signals for subsequent processing. An image reconstructor 25, receives sampled and digitized x-ray data from the DAS 24 and performs high speed image reconstruction. The reconstructed image is applied as an input to a computer 26 which stores the image in a mass storage device 29.

The computer 26 also receives commands and scanning parameters from an operator via a console 30 that has a keyboard. An associated display 32 allows the operator to observe the reconstructed image and other data from the computer 26. The operator supplied commands and parameters are used by the computer 26 to provide control signals and information to the DAS 24, the x-ray controller 22 and the gantry motor controller 23. In addition, computer 26 operates a table motor controller 34 that controls a motorized table 36 to position the patient 15 in the gantry 12.

The above-described third generation CT system may be operated in a dual energy mode while performing a scan. More particularly, at each view angle the x-ray controller 22 operates the x-ray sources 13 to acquire both a low energy transmission profile and a high energy transmission profile. This is accomplished by switching the anode voltage on the x-ray sources 13 between two levels that produce the prescribed x-ray energy levels. The transmission profile views for each energy level are separately stored and processed as described in more detail below. In the alternative, the x-ray controller 22 operates one x-ray source 13 at one anode voltage and the second x-ray source 13 at another anode voltage (e.g., 80 kv and 140 kv). In this way, both a low energy and high energy image can be acquired in one acquisition.

Figure 3:
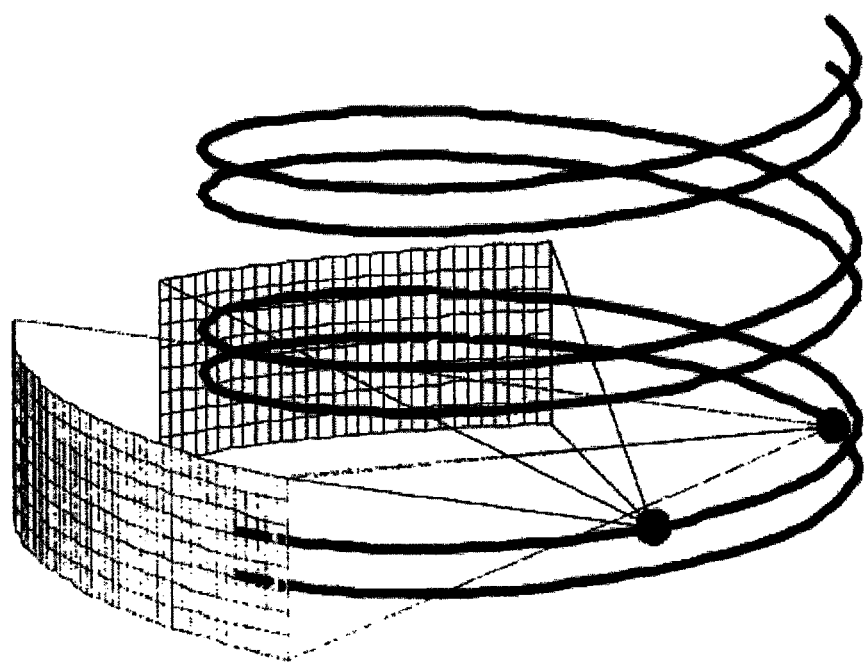
FIG. 3 is a pictorial example of a dual-source, helical scan trajectory employed by the CT imaging system of FIGS. 1 and 2.

When operating in a dual-energy helical scan mode, data is acquired as two sets of non-coincident projections views, as shown in FIG. 3. This presents a problem for the above-described, pre-reconstruction quantitative CT methods, such as the basis-material method described above. Since no projection views in the high- and low-energy data sets are coincident with each other, decomposition of the acquired data into basis materials is not possible. In order to provide a method for basis-material decomposition for projection space data acquired in a helical scan mode, an interpolation method, such as the 180LI method for single-slice CT or extended interpolation methods for multi-slice helical CT, is used to first convert the two sets of helical data into two sets of circular fan-beam, or cone-beam, data at any slice location.

The method of the present invention may include the application of z-axis spiral interpolation algorithms to the two helical projection data sets, where corresponding projections of the high- and low-energy datasets are shifted with respect to one another by 90 degrees and another angles. A dual-source helical interpolation algorithm allows for projection space dual-energy processing by realigning the high- and low-energy datasets based on the z-axis interpolation. This complex algorithm can be implemented using a variety of interpolation schemes. These can be extended from single slice to multi-slice data acquisitions. A variety of helical rebinning algorithms can be employed, depending on the number of slices and the accuracy of the interpolation algorithms, such as the methods described by Crawford and King in "Computed Tomography Scanning with Simultaneous Patient Translation," Medical Physics (1990); 17:967-982, and Taguchi and Aradate in "Algorithm for image reconstruction in multi-slice helical CT," Medical Physics (1998); 25:550-561, and Defrise and Liu in "A fast rebinning algorithm for 3D positron emission tomography using John's equation," Inverse Problems (1999); 15:1047-1065 and incorporated herein in its entirety by reference.

Figure 4:
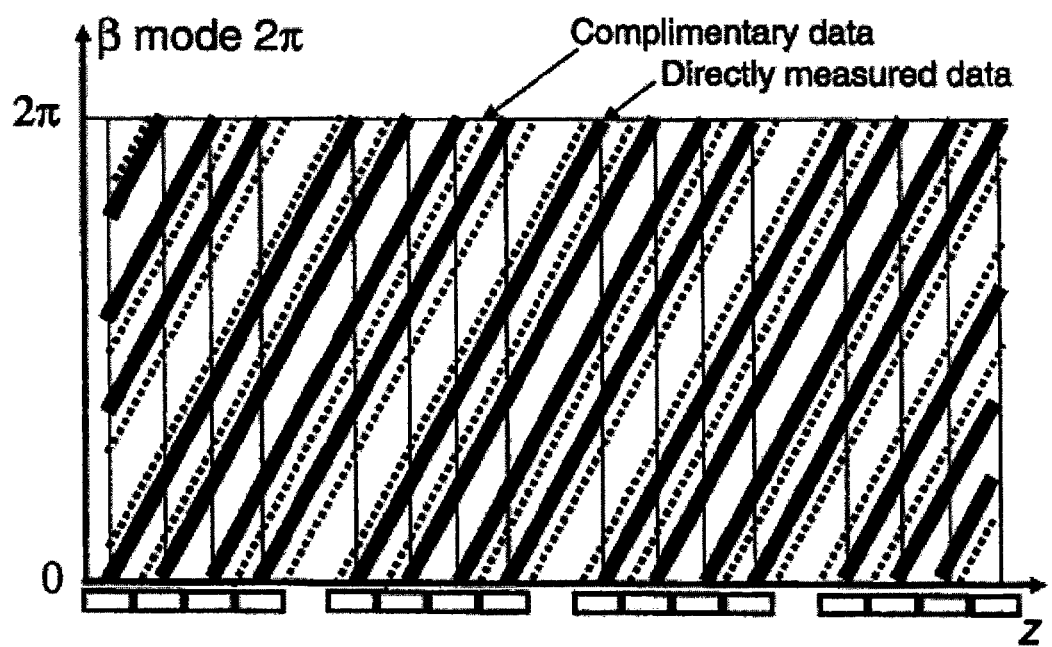
FIG. 4 is a diagram of an exemplary interpolation method for helical projection data sets.

An example of the 180LI method applied to a four slice helical data set is shown in FIG. 4. Since the 180LI helical interpolation method neglects the cone-beam angle effect, the interpolation will lead to cone-beam artifacts when the number of detector rows increases. The method works for up to eight detector rows before a different interpolation method is preferably employed. Subsequent to the registration of the dual-energy data, projection space processing allows for virtual monochromatic images in which the beam hardening artifact has been substantially suppressed.

Figure 5:
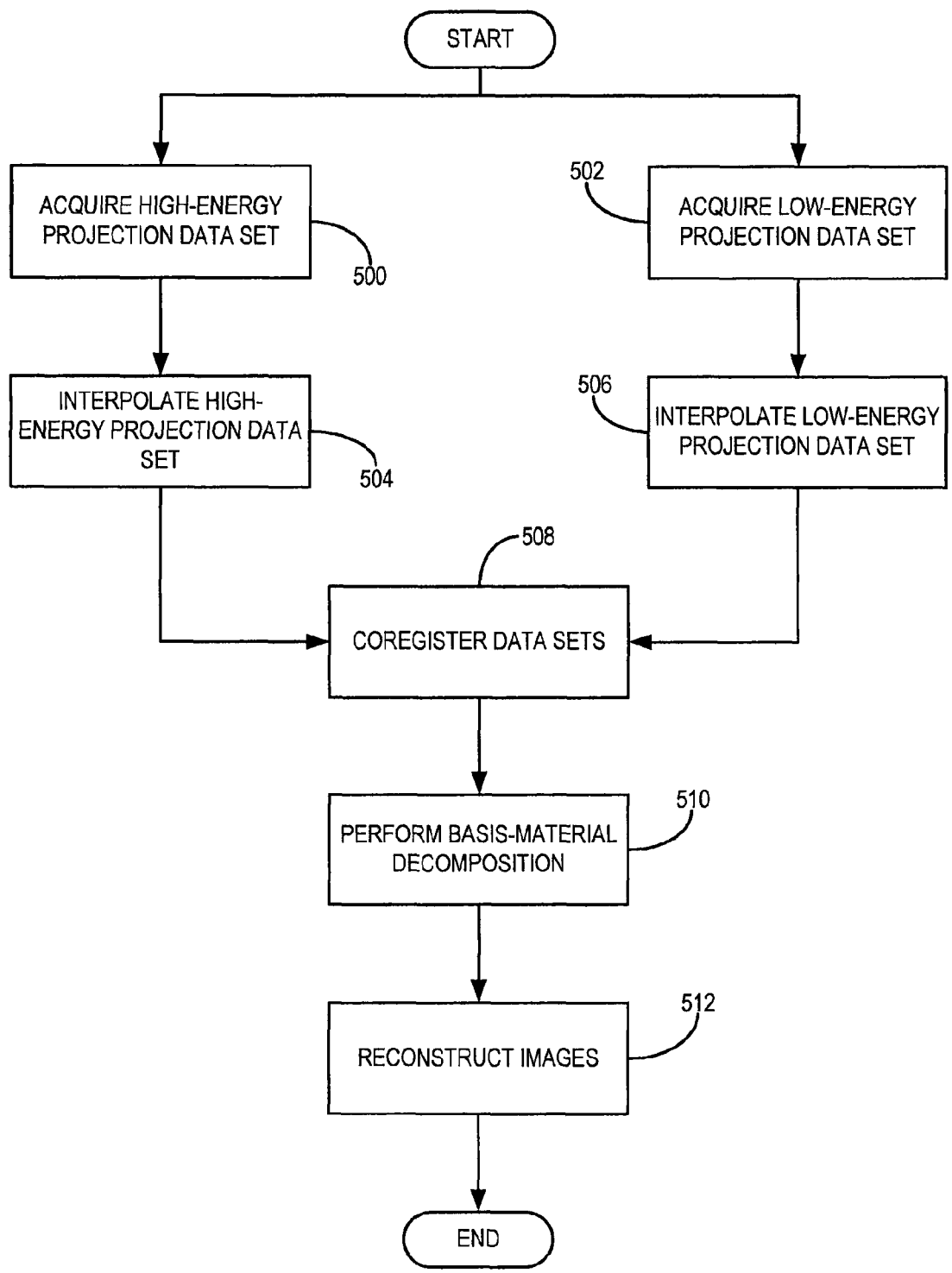
FIG. 5 is a flowchart showing the steps of the method of the present invention employed by the CT imaging system of FIGS. 1 and 2.

Referring particularly to FIG. 5, a method of the present invention begins by acquiring a high- and low-energy projection data set, as indicated at steps 500 and 502, respectively. Each projection data set is acquired substantially contemporaneously as the subject is moved through the bore of the DSCT imaging system. As indicated above, in the dual-source arrangement, no projection view in the high-energy projection data set is coincident with any projection view in the low-energy projection data set. As a result, the high- and low-energy helical projection data sets are interpolated into a series of circular projection data sets, as indicated in steps 504 and 506, respectively. The high- and low-energy circular projection data sets are subsequently coregistered in step 508. By coregistering the two circular projection data sets, accurate quantitative CT methods can now be utilized because the two data sets now include coincident projection views. Accordingly, a basis-material decomposition of the high- and low-energy circular projection data sets is performed at step 510 in accordance with equation (2) discussed above. After determining the density values, $\rho_1(r)$ and $\rho_2(r)$, for the two basis materials, images indicative of the corresponding materials are reconstructed using conventional CT image reconstruction methods, as indicated at step 512. Furthermore, monochromatic images of the two materials may be reconstructed at any x-ray energy using known mass attenuation coefficients and the relationship provided in equation (1). By looking up the mass attenuation coefficients for the two materials in a table and using those values as a weighting factor for the density values determined in step 510, the linear attenuation coefficient at any energy can be determined and subsequently employed to produce further images of the materials.

While the present invention has been described with respect to determining the basis-material decomposition of only two materials, it can appropriately be employed when performing basis-material decomposition of more than two materials. In such instances, a method such as the one disclosed in co-pending U.S. Patent Application Ser. No. 61/029, 125, entitled "System and Method for Quantitative Imaging of Chemical Composition to Decompose More Than Two Materials," which is incorporated herein in its entirety by reference, may be employed. Moreover, it will be appreciated by those skilled in the art that other pre-reconstruction quantitative CT methods can be similarly employed instead of basis-material decomposition methods.

Provided as an example of practicing the present invention, two sets of helical scan data (one corresponding to an x-ray source energy of 140 kV and the other of 80 kV) are acquired with a dual-source single-slice scanning configuration using titanium and aluminum filtration of the x-ray beams. As described above, the phase difference between the two sources is 90 degrees. For the high-energy x-ray source, the mAs is set to 160, while for the low-energy x-ray source, the mAs is set to 910. The data are converted to two sets of circular fan-beam projection data at each slice location using the 180LI interpolation method. Using water and bone as basis materials, equation (2) is solved to determine the sinograms of bone and water density.

The present invention has been described in terms of one or more embodiments, and it should be appreciated that many equivalents, alternatives, variations, and modifications, aside from those expressly stated, are possible and within the scope of the invention.

The invention claimed is:

1. A method for producing an image with a computed tomography (CT) imaging system, the method comprising the steps of:
    a) acquiring a first helical, projection data set using a first-energy x-ray source traversing a helical trajectory along a longitudinal axis of a subject;
    b) acquiring a second helical, projection data set using a second-energy x-ray source traversing a helical trajectory along the longitudinal axis of the subject, wherein the first-energy x-ray source and the second-energy x-ray source deliver x-ray energy at differing energy levels;
    c) transforming the first helical, projection data set into a first non-helical, projection data set;
    d) transforming the second helical, projection data set into a second non-helical, projection data set;
    e) registering the first non-helical, projection data set with the second non-helical, data set; and
    f) reconstructing, from the registered first and second non-helical, projection data sets, at least one image indicative of a basis-material decomposition within the subject.

2. The method of claim 1 wherein the at least one image indicative of a basis-material decomposition includes bone.

3. The method of claim 1 wherein the at least one image indicative of a basis-material decomposition includes water.

4. The method of claim 1 wherein step f) includes performing a basis-material decomposition.

5. The method of claim 1 wherein the first projection data set and the second projection data set are related as:

$$I_k = \int S_k(E) \cdot D(E) \cdot E \cdot e^{-\left[\left(\frac{\mu}{\rho}\right)_1(E) \cdot L_1 + \left(\frac{\mu}{\rho}\right)_2(E) \cdot L_2\right]} dE,$$

where $S_k(E)$ is an x-ray spectrum for the $k^{th}$ x-ray energy, $D(E)$ is a detector response, $L_1 = \int dl \cdot \rho_1(r)$, and $L_2 = \int dl \cdot \rho_2(r)$, which represent a line integral of densities of two basis materials.

6. The method of claim 1 wherein the first non-helical, projection data set and the second non-helical, data set are circular fan-beam projection data sets.

7. The method of claim 1 wherein the first-energy x-ray source and the second-energy x-ray source are the same x-ray source.

8. The method of claim 1 wherein the first-energy x-ray source and the second-energy x-ray source are different x-ray sources.

9. The method of claim 1 wherein, prior to step f), projection space processing is performed for virtual monochromatic images to substantially suppress beam hardening artifacts in the at least one image.

10. A method of processing projection data acquired with a dual-source computed tomography (DSCT) imaging system, the method comprising the steps of:
    a) acquiring a helical, high-energy projection data set using a high-energy x-ray source traversing a helical trajectory along a longitudinal axis of a subject;
    b) acquiring a helical, low-energy projection data set using a low-energy x-ray source traversing a helical trajectory along the longitudinal axis of the subject;
    c) transforming the helical high-energy projection data set into a non-helical high-energy projection data set;

d) transforming the helical low-energy projection data set into a non-helical low-energy projection data set;
e) registering the non-helical high-energy projection data set with the non-helical low-energy data set;
f) performing a basis-material decomposition on the registered projection data sets to create a decomposition data set; and
g) reconstructing, from the decomposition data set, an image indicative of a selected material within the subject.

11. The method of claim 10 wherein step f) includes reconstructing, from the decomposition data set, at least one image indicating multiple selected materials.

12. The method of claim 11 wherein the multiple selected materials include bone and water.

13. The method of claim 10 wherein the non-helical projection data sets are circular fan-beam projection data sets.

14. The method of claim 10 wherein the low-energy x-ray source and the high-energy x-ray source are different x-ray sources.

15. The method of claim 10 wherein, prior to step g) projection space processing is performed for virtual monochromatic images to substantially suppress beam hardening artifacts within the image indicative of the selected material within the subject.

16. The method of claim 10 wherein step a) includes using a first source of the DSCT imaging system and step b) includes using a first source of the DSCT imaging system and, wherein the first source and the second source are different sources.

* * * * *